United States Patent [19]

Brandman et al.

[11] 4,206,229

[45] Jun. 3, 1980

[54] PRESERVATION OF AQUEOUS SYSTEMS WITH $\alpha$-BROMO-$\beta$-AMINOCROTONONITRILE

[75] Inventors: Harold A. Brandman, Glen Ridge; Milton Manowitz, Wayne; David L. Coffen, Glen Ridge, all of N.J.

[73] Assignees: Givaudan Corporation, Clifton; Hoffmann-La Roche, Inc., Nutley, both of N.J.

[21] Appl. No.: 934,310

[22] Filed: Aug. 17, 1978

[51] Int. Cl.$^2$ .............................................. A01N 9/20
[52] U.S. Cl. ................................... 424/304; 252/49.5; 252/51; 252/401; 260/465.5 R
[58] Field of Search ................. 424/304; 252/49.5, 51, 252/401; 260/465.5 R

[56] References Cited

PUBLICATIONS

Ohoka et al.; J. Org. Chem., 38 (13), 2287 (1973).

*Primary Examiner*—Allen J. Robinson
*Attorney, Agent, or Firm*—Robert F. Tavares; Thomas Cifelli, Jr.

[57] ABSTRACT

Methods and compositions for inhibiting or preventing the growth of microorganisms in aqueous systems wherein the growth is inhibited or prevented by the presence of an effective amount of $\alpha$-bromo-$\beta$-aminocrotononitrile.

6 Claims, No Drawings

PRESERVATION OF AQUEOUS SYSTEMS WITH α-BROMO-β-AMINOCROTONONITRILE

THE INVENTION

A number of aqueous systems are susceptible to antimicrobial growth. Among these are cosmetics latex paints, polymer emulsions and other oil water emulsions, cutting oils, adhesives, water used in industrial cooling towers, white water in the paper mills and the like. The growth of bacteria and fungi in such systems can be a serious problem if not properly controlled. For example, industrial aqueous systems are susceptible to slime formation which, if unchecked, can cause severe maintainance and production problems. Similarly, consumer products such as cosmetics can be damaged by the growth of bacteria, fungi or algae.

There is, consequently, a continuing need to provide effective and economical antimicrobial agents which protect these systems. The finding of this invention is that compositions and methods utilizing α-bromo-β-aminocrotononitrile provide effective control of such microbial growth. The α-bromo-β-aminocrotononitrile has been found effective against a broad spectrum of bacteria including gram positive bacteria, gram negative bacteria and fungi. The breadth of such activity is illustrated in the examples.

The α-bromo-β-aminocrotononitrile used in this invention is described in the literature. See, for example, M. Ohoka et al. J. Org. Chem. 38 (13), 2287 (1973).

DESCRIPTION OF THE PREFERRED EMBODIMENTS

The α-bromo-β-aminocrotononitrile may be added to the aqueous systems or formulations as is or dissolved in organic solvents such as alcohols, acetone, dimethylformamide and the like. It may be added alone or in combination with other biocides and/or functional compounds such as antioxidants, anticorrosive agents, surfactants, etc.

Concentrations from about 0.005 to above 0.3% are effective. Use of larger concentrations, while feasible, is recommended only for unusual applications. It is preferred to use concentrations from about 0.01% to about 0.2%.

The α-bromo-β-aminocrotononitrile can be used as a preservative for oil in water emulsions. A number of oil in water emulsions are used in industry, for example in the high speed metal working and textile industries, for their cooling, lubricating, antistatic and anticorrosive properties. Unless adequately protected by an effective preservative, such systems are susceptible to bacterial decomposition producing obnoxious odors and potential hazards. [Detailed descriptions of these systems, their microbiological problems and difficulties in their preservation can be found in: Bennet, E. O., Soap Chem. Specialties, 32, 46 (1956). Fabian, F. W. & Pivnick, H., Applied Microbiology, 1, 201 (1953)].

In practicing the invention, the active ingredient may be added by directly dissolving it in the concentrated cutting oil which is then diluted with water to form the cutting oil emulsion. It may also be added to the final emulsion as a liquid or dissolved in a solvent such as dimethylformamide, alcohol, acetone, etc. Similar methods known in the art for adding preservatives to such oil and water emulsions may also be used.

There can be used as little as about 0.005%. Although amounts greater than 0.3% are operable, they are recommended only for unusual applications. It is preferred to use amounts in the range of from about 0.01% to about 0.20%, with amounts in the range of about 0.02% to 0.10% being especially preferred.

The α-bromo-β-aminocrotononitrile is particularly effective as a cosmetic preservative [Problems encountered in the preservation of cosmetics are described by Dunnigan, A. P., Drug and Cosmetic Industries, 103, 43, (1968)].

The compound may be added to the finished cosmetic product directly or dissolved in suitable solvents such as alcohol, acetone, dimethyl formamide, etc. alternatively the compounds may be dissolved in the oils or other raw materials used in the formula and then formulated in the final product.

In cosmetic preparations, concentrations as low as 0.01% are found to be operable. Concentrations greater than 0.30%, while operable, are recommended only for unusual applications. Concentrations in the range of from about 0.01% to about 0.20% are preferred with concentrations of about 0.05% to 0.10% being especially preferred.

ILLUSTRATION OF PREFERRED EMBODIMENTS

A number of examples are provided herein to illustrate the preferred embodiments of this invention. The examples provided are included for the sole purpose of illustrating the preferred embodiments and should not be construed as limiting. They are intended to embrace any equivalents or obvious extensions which are known or should be known to a person skilled in the art.

EXAMPLE I

General Antimicrobial Activity

The α-bromo-β-aminocrotononitrile is active against a wide variety of microorganisms as illustrated below.

A 6% solution of α-bromo-β-aminocrotononitrile in dimethyl formamide was prepared. The 6% solution was then 5-fold serially diluted in test tubes to give the desired concentrations when mixed with agar and poured into sterile Petri dishes. For instance, 0.8 ml of a 6% stock solution plus 24.2 ml of agar gives a test concentration of 1920 mcg/ml, the highest level tested. Tryptone glucose extract agar is used for the bacterial testing; mildew glucose agar for the fungal testing. The bacterial plates were spot inoculated with 24-hour nutrient broth cultures and incubated at 37° C. for 48 hours. The fungal plates were spot inoculated with spore suspensions and incubated at 28° C. for seven days. At the end of the incubation periods, all plates were examined for growth. The minimum inhibitory concentration (MIC) for each organism is expressed in Table I. In the ranges presented, growth is observed only at the lower concentration.

TABLE I

| Bacteria | Minimum Inhibitory Concentration Range |
|---|---|
| Staphylococcus aureus | 384 µg/ml–1920 µg/ml |
| Escherichia coli | 384 µg/ml–1920 µg/ml |
| Pseudomonas aeruginosa | 384 µg/ml–1920 µg/ml |
| Proteus vulgaris | 384 µg/ml–1920 µg/ml |
| Bacillus subtilis | 384 µg/ml–1920 µg/ml |
| Fungi | |
| Aspergillus niger | 15 µg/ml–76µg/ml |
| Aspergillis oryzae | 15 µg/ml–76 µg/ml |
| Penicillium piscarium | 15 µg/ml–76 µg/ml |

TABLE I-continued

| Bacteria | Minimum Inhibitory Concentration Range |
|---|---|
| *Aureobasidium pullulans* | 76 µg/ml–384 µg/ml |

EXAMPLE II

Utility as a Cosmetic Preservative

The α-bromo-β-aminocrotononitrile is an effective cosmetic preservative. Two-fold serial dilutions of 6% solutions of the α-bromo-β-aminocrotononitrile in dimethylformamide were added to a cosmetic lotion of the following formulation:

| | | |
|---|---|---|
| Stearic acid | | 1.4 g |
| Mineral Oil | | 2.3 g |
| Arlacel 60 | (sorbitan monostearate) | 0.7 g |
| Tween 20 | [Polyoxyethylene (20) sorbitan monostearate] | 1.6 g |
| Distilled water | | 94.0 g |

The lotions were inoculated with both *Pseudomonas aeruginosa* and *Aspergillus niger* and incubated at 28° C. At weekly intervals, the lotions were examined for microorganisms by conventional streak-plate methods or by macroscopic observation. The lotions were then reinoculated with the test organisms and reincubated. Table II shows the minimum inhibitory concentration that was effective in preventing microbial growth for the four week period.

TABLE II

| | Minimum Inhibitory Concentration Range (micrograms/milliliter) | |
|---|---|---|
| Week | *Psuedomonas aeruginosa* | *Aspergillus niger* |
| 1 | 250–500 µg/ml | <125 µg/ml |
| 2 | 125–250 µg/ml | <125 µg/ml |
| 3 | 125–250 µg/ml | <125 µg/ml |
| 4 | 125–250 µg/ml | <125 µg/ml |

Utility as a Preservative for Oil in Water Emulsions

The utilities of the α-bromo-β-aminocrotononitrile in water and oil emulsions is illustrated below utilizing a commercially available cutting oil. The data of Table III clearly illustrate its effectiveness.

In running these tests, two-fold serial dilutions of 6% solutions of the compound in dimethylformamide was added to 3.3% cutting oil emulsions. The emulsions were prepared by diluting with water a commercially available cutting oil concentrate. The emulsions were inoculated with a culture of *Pseudomonas aeruginosa* and incubated at 28° C. on a rotary shaker. At weekly intervals, the emulsions were examined for bacteria by conventional streak-plate methods. The emulsions were then reinoculated with *Pseudomonas aeruginosa* and reincubated.

TABLE III

| | Minimum Inhibitory Concentration Range (micrograms/milliliter) |
|---|---|
| Week | *Psuedomonas aeruginosa* |
| 1 | 125–250 µg/ml |
| 2 | 125–250 µg/ml |
| 3 | 125–250 µg/ml |
| 4 | 125–250 µg/ml |

We claim:

1. A method of inhibiting or preventing the growth of bacteria and fungi in an aqueous composition subject to spoilage thereby which comprises incorporating in said composition an amount of α-bromo-β-aminocrotononitrile effective to inhibit or prevent such growth.

2. A method according to claim 1 wherein the α-bromo-β-aminocrotononitrile is utilized at a level of from about 0.005% to about 0.3%.

3. A method according to claim 2 wherein the amount utilized is from about 0.01% to about 0.2%.

4. The method of claim 1 wherein the composition to be protected is a cosmetic formulation.

5. The method of claim 1 wherein the composition to be protected is a water and oil emulsion.

6. The method claim 5 wherein the composition to be protected is a cutting oil.

* * * * *